United States Patent [19]
Posner

[11] Patent Number: 6,017,946
[45] Date of Patent: Jan. 25, 2000

[54] SEROTONIN CONTAINING FORMULATION FOR ORAL ADMINISTRATION AND METHOD OF USE

[76] Inventor: Robert Posner, 11204 Devereuc Manor, Fairfax Station, Va. 22309

[21] Appl. No.: 09/052,135

[22] Filed: Mar. 31, 1998

Related U.S. Application Data

[60] Provisional application No. 60/061,336, Oct. 8, 1997.
[51] Int. Cl.$^7$ .................................................. A61K 31/00
[52] U.S. Cl. .......................... 514/415; 514/408; 514/410; 514/412; 514/814
[58] Field of Search ..................................... 514/253, 277, 514/419, 474, 814, 408, 410, 412, 415

[56] References Cited

U.S. PATENT DOCUMENTS

| | | | |
|---|---|---|---|
| 3,883,554 | 5/1975 | Mori et al. ..................... | 280/326.14 T |
| 4,582,719 | 4/1986 | Kaetsu et al. .................. | 427/2 |
| 4,596,807 | 6/1986 | Crosby ........................... | 514/277 |
| 5,032,578 | 7/1991 | Horovitz ......................... | 514/19 |
| 5,521,196 | 5/1996 | Audia et al. ................... | 514/323 |
| 5,653,987 | 8/1997 | Modi et al. .................... | 424/400 |

*Primary Examiner*—Michael P. Woodward
*Assistant Examiner*—C. Delacroix-Muirheid

[57] ABSTRACT

A medicament containing serotonin and an antioxidant useful in the treatment of pain, including migraines and premenstrual syndrome(PMS); chronic fatigue symptoms; depression and eating disorders; and a method for increasing the serotonin level in humans by orally administering a composition containing serotonin and an antioxidant in an amount effective to prevent oxidation or degradation of the serotonin in the gastrointestinal tract are herein described.

11 Claims, No Drawings

SEROTONIN CONTAINING FORMULATION FOR ORAL ADMINISTRATION AND METHOD OF USE

CROSS REFERENCE TO RELATED APPLICATIONS

This application claims priority from U.S. Provisional Patent Application Ser. No. 60/061,331, entitled "Serotonin Containing Formulation for Oral Administration and Method of Use", filed on Oct. 8, 1997. The disclosure of that provisional patent application is incorporated herein by reference in its entirety.

FIELD OF THE INVENTION

This invention relates, in general, to the oral administration of serotonin. The serotonin containing compositions are useful in controlling pain such as in migraine headaches, premenstrual syndrome(PMS), eating disorders, and depression in animals. This invention further relates to a method of controlling pain, eating disorders, chronic fatigue and depression in animals by orally administering the medicinal compositions of this invention or components thereof The invention also relates to the method of co-administering the compositions of this invention or components thereof with an antioxidant such as vitamins to achieve potentiation of the effects of the serotonin.

BACKGROUND OF THE INVENTION

Serotonin (5-hydroxytryptamine or 5-HT) is present in animals, plants, fruits, and nuts. Inside the body, serotonin is produced from an amino acid, tryptophan. Serotonin is formed in the body by hydroxylation and decarboxylation of the essential amino acid L-tryptophan. In the biosynthesis of serotonin from L-tryptophan, L-tryptophan is hydroxylated in the presence of the enzyme tryptophan hydroxylase to form the intermediate product L-5-hydroxytryptophan (L-5-HTP). This intermediate product is decarboxylated in the presence of the enzyme 5-hydroxytryptophan decarboxylase to form serotonin. By the term "serotonin precursor" is intended L-tryptophan, L-5-hydroxytryptophan, pharmacologically equivalent analogues of L-trytophan and L-5-hydroxytryptophan and pharmaceutically acceptable salts of L-tryptophan and L-5-hydroxytryptophan.

Serotonin or serotonin deficiency has been implicated in the treatment or the cause of various medical disorders including depression, premenstrual syndrome, migraine headaches and obesity. To date medications or "homeopathic" preparations attempt to raise serotonin levels inside the body act by inhibiting serotonin uptake systems or increasing the endogenous production of serotonin. It has recently been implicated that the oral administration of certain serotonin precursors or artificial serotonin production facilitators results in harmful side effects, such as eosinophilic-myalgia syndrome, heart valve disfunction and pulmonary hypertension.

It has previously been believed that oral administration of serotonin was not therapeutically effective since serotonin was readily oxidized in the gastrointestinal tract thereby derivatizing the serotonin into non-therapeutic compositions. Therefore "serotonin precursors", such as L-tryptophan, capable of being transformed into serotonin in the body have been orally administered for the treatment of various medical conditions.

It is therefor desirable to orally administer serotonin without using serotonin precursors in a manner effective to administer serotonin into the bloodstream.

SUMMARY OF THE INVENTION

The present invention relates to an oral medicament containing serotonin and an antioxidant useful in the treatment of pain, including migraines and premenstrual syndrome(PMS); chronic fatigue symptoms; depression and eating disorders. The present invention also relates to a method for increasing the serotonin level in a human having a reduced serotonin level in their bloodstream by orally administering a composition containing serotonin in an amount effective to increase the serotonin level present in the bloodstream to a supranormal level, in combination with an antioxidant in an amount effective to prevent oxidation or degradation of the serotonin in the gastrointestinal tract.

DESCRIPTION OF THE PREFERRED EMBODIMENTS

The present invention relates to an oral medicament containing a combination of serotonin or an equivalent amount of the pharmaceutically acceptable salt thereof and an antioxidant. This medicament is preferably enterically coated. This composition is useful for the treatment of pain, including migraines and premenstrual syndrome(PMS); chronic fatigue symptoms; depression and eating disorders.

Typical unit dosage forms or therapeutically effective amounts contain 0.01 to 1.5 mg, preferably 0.05 to 0.5 mg, of the serotonin, this dosage being in an amount effective to increase the serotonin level in the bloodstream, particularly in the brain, to a supranormal level after oral administration, and 20 to 1000 mg of the antioxidant, preferably vitamin C or vitamin E as well as pharmaceutically acceptable salt of these vitamins. The antioxidant is used in an amount that prevents oxidation and degradation in the gastrointestinal tract of an amount of serotonin in the dosage form to increase the serotonin level in the bloodstream to a supranormal level after ingestion. Supranormal levels are well known to those skilled in the art.

The active ingredient, serotonin, is admixed with one or more antioxidants including but not limited to: vitamin A, vitamin E, and vitamin C as well as pharmaceutically acceptable salt of these vitamins; selenium, red wine, beta-carotene, curcumin, rosemary extract, ginger, grapeseed extract, pine bark extract, green tea leaves, butylated hydroxyanisole, butylated hydroxytoluene or mixtures thereof Preferred compositions contain, 1 to 20 parts by weight of the serotonin, and 50 to 10,000 parts by weight of at least one antioxidant, preferably vitamin C or vitamin E as well as pharmaceutically acceptable salt of these vitamins.

The composition of the invention typically preferably contains one or more additional vitamins such as thiamine, riboflavin, niacin, vitamin $B_6$, vitamin $B_1$, and the like as well as a source of calcium such as calcium phosphate or calcium carbonate. When present, such other vitamins are typically present in an amount of at least about 80% of the U.S. Recommended Daily Allowance (RDAs) per dose of composition, more typically at least about 90% of the RDAs per dose of composition, and preferably at least about 100% of the RDAs per dose of composition. It is recognized that the daily dose recommended by nutritional experts may change. A typical dose of composition is one to two grams. The current RDAs for selected vitamins and calcium are as follows:

| | |
|---|---|
| vitamin A | 1500 IU |
| vitamin D | 400 IU |
| vitamin B | 5 IU |
| vitamin C | 35 mg |
| thiamine | 0.5 mg |
| riboflavin | 0.6 mg |
| niacin | 8 mg |
| vitamin $B_6$ | 0.4 mg |
| vitamin $B_{12}$ | 2 mug |
| calcium | 1000 mg |

Those skilled in the art appreciate that appropriate additional amounts (overages) of vitamin ingredients including the antioxidants need to be provided to compensate for some loss during storage of the serotonin-vitamin, dietary supplement, or therapeutic formulations of the present invention.

The present invention displays a method for treatment of pain, including migraines and premenstrual syndrome (PMS), chronic fatigue symptoms, depression and eating disorders in an animal such as humans by orally administering to the subject a composition containing serotonin in an amount effective to increase the brain and/or bloodstream serotonin to a supranormal level, i.e 21 to 320 nanograms per ml of blood, in combination with an antioxidant in an amount effective to prevent oxidation of an amount of the serotonin effective to increase the brain serotonin to a supranormal level. Thus the antioxidant must be incorporated into the formulation in an amount that prevents oxidation of the serotonin in the gastrointestinal tract of at least a pharmaceutically effective amount of the serotonin. In order to accomplish the administration of serotonin into the human bloodstream and into the brain, it is preferable to use an enteric coating on tablets used in the oral administration of the serotonin. The use of the enteric coating assists in preventing the premature oxidation of the serotonin by gastric juices.

The serotonin-vitamin, dietary supplement, and pharmacological formulations of the invention can be prepared by standard techniques known in the art. As appreciated by the skilled artisan, the desired processing technique will vary depending upon the exact types and amounts of vitamins present, nature and amount of surfactant, processing temperature, and the like.

In addition to the therapeutically active compounds, the new therapeutic preparations usually contain suitable excipients and auxiliaries which facilitate processing of the active compounds into preparations which can be used pharmaceutically. The preparations of the present invention are administered orally by normally preferred types of administration, such as tablets, dragees, and capsules, and contain from about 0.1 to 99%, preferably from about 25–85%, of active compound(s), together with the excipient.

The therapeutic preparations of the present invention are manufactured in a manner which is in itself known, for example, by means of conventional mixing, granulating, dragee-making, dissolving, or lyophilizing processes. Thus, therapeutic preparations for oral use can be obtained by combining the active compounds with solid excipients, optionally granulating a resulting mixture and processing the mixture or granules, after adding suitable auxiliaries, if desired or necessary, to give tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders, such as starch, pastes, using, for example, maize starch, wheat starch, rice starch, or potato starch, gelatine, tragacanth, methyl cellulose, hydroxypropylmethyl cellulose, sodium carboxymethyl cellulose, and/or polyvinyl pyrrolidone, cross-linked polyvinyl pyrrolidone, agar or algenic acid or a salt thereof, such as sodium aliginate. Auxiliaries are, above, all, flow-regulating agents and lubricants, for example, silica, talc, stearic acid or salts thereof, such as magnesium stearate or calcium stearate, and/or polyethylene glycol.

The tablet compositions and the dragee cores are preferably provided with suitable coatings including enteric coatings, which are resistant to gastric juices. In order to produce enteric coatings resistant to gastric juices, solutions of suitable cellulose preparations, such as acetyl cellulose phthalate or hydroxypropylmethyl cellulose phthalate, are used to form the enteric coatings as are well known to those skilled in the art. These coatings optionally contain other ingredients such as gum Arabic, talc, polyvinyl pyrrolidone, polyethylene glycol, titanium dioxide, and lacquer.

Dyestuffs or pigments may be added to the tablets or dragee coatings, for example, for identification or in order to characterize different combinations of active compound doses.

Other forms of administration of the therapeutically effective preparations include push-fit capsules made of gelatin. The push-fit capsules can contain the active compounds including the serotonin and the antioxidants, preferably in the form of granules, for example, mixed with fillers such as lactose, binders such as starches, and/or lubricants such as talc or magnesium stearate and, optionally, stabilizers.

The oral dosage compositions of the present invention, in and of themselves, find utility in the control of pain, both mild and severe, be it chronic or acute, including migraine headaches and premenstrual syndrome(PMS). Additionally, the compositions of this invention find utility in the treatment of symptoms of chronic fatigue, depression and eating disorders.

Serotonin is the natural calming, mood-regulating neurotransmitter synthesized by the body in vivo. The compounds of the present invention direct the body's own mechanism for dealing with pain, chronic fatigue and depression to its maximum functional potential.

Additionally, a low potency version is useful in the management of mild or chronic pain alone or supplemented by narcotics. This same low potency version is useful in the management of migraines and chronic headaches.

Further, it is possible that the compositions of the present invention are useful in the management of chronic severe pain such as the pain associated with metastatic disease, neurologic disease such as myofascial pain, and the like.

The effects achieved with the oral administration of the compositions of the present invention may not be immediate and certain patients may require five to seven days of treatment to begin responding favorably. After two weeks of therapy, most patients will respond well and near maximal effects will be noted at four to six weeks of continued therapy. And, unlike narcotics, uninterrupted long-term therapy will not be met with tolerance to the therapy according to the present invention, but rather, even superior results appearing as therapy continues.

The compositions of the present invention may be orally administered by any means that effect pain management, control of depression and chronic fatigue symptoms, and eating disorders. The dosage administered will be dependent upon the age, health, and weight of the recipient, kind of concurrent treatment, if any, frequency of treatment, and the nature of the effect desired.

Administration of the composition is desirably effected in from 1 to 4 portions daily, preferably by oral administration, e.g. liquids, capsules, or tablets. Each dosage unit will contain 0.01 to 1.5 mg of the serotonin, and 20 to 1000 mg of an antioxidant, preferably vitamin C.

The present invention will be described in more detail with reference to non-limitative examples. The following examples are presented for purposes of illustration only and are not to be construed in a limiting sense.

EXAMPLES

The following study was designed to evaluate both the ability to effectively deliver by oral administration, a serotonin containing vitamin/dietary supplement in the form of a tablet containing either of the compositions as displayed in Formulations 1 and 2 and the efficacy of these orally administrable therapeutic preparations in helping mild to moderate depression, premenstrual syndrome, and/or migraine headaches. These tableted formulations were enterically coated with Eudragit L100-55.

| FORMULATION 1 | |
|---|---|
| serotonin | 100 micrograms |
| thiamine hydrochloride | 0.81 milligrams |
| riboflavin | 0.92 milligrams |
| pyridoxine hydrochloride | 1.08 milligrams |
| cyanocobalamine | 3.2 micrograms |
| vitamin C | 162 milligrams |
| vitamin E | 16 IU |
| niacinamide | 11 milligrams |
| calcium | 135 milligrams |
| Eudragit L100-55 | 52.5 milligrams |
| magnesium stearate | 1.5 milligrams |
| dicalcium phosphate | qs 850 milligrams |

| FORMULATION 2 | |
|---|---|
| serotonin | 100 micrograms |
| thiamine | 1.8 milligrams |
| riboflavin | 2.13 milligrams |
| pyridoxine hydrochloride | 3.03 milligrams |
| cyanocobalamine | 0.78 milligrams |
| vitamin C | 120 milligrams |
| vitamin E | 72 milligrams |
| vitamin A | 180 milligrams |
| niacinamide | 22 milligrams |
| calcium pantothenate | 19.62 milligrams |
| Eudragit L100-55 | 27 milligrams |
| magnesium stearate | 15 milligrams |
| maltodextrin | qs 540 milligrams |

Eight human female subjects, ranging in age from 33 to 49, each displaying subjective symptoms of mild-moderate depression, premenstrual syndrome and/or migraine headaches, orally took one of the serotonin vitamin/dietary supplements, exemplified by either Formulation 1 or Formulation 2, each day for 60 days with breakfast. After six week of treatment the following are the results of these treatments as determined by questionnaire or laboratory testing:

Six of the eight subjects noted a subjective improvement in their depressive symptoms as noted in the Zung Depression Scale questionnaire. Seven of the eight subjects noted a subjective improvement in their premenstrual symptoms. Of the seven subjects having histories of migraine headaches, six of these subjects displayed improvement in the form of decreased frequency and/or decreased intensity in their headaches.

There were no changes in the "pre" and "post" blood pressures, pulses, and physical examinations in each subject. There were no changes in the "pre" and "post" complete blood counts, chemistry profiles, and thyroid panels in each subject. The four subjects that had "pre" and "post" serotonin blood levels measured, displayed serotonin blood level changes over 20% from the baseline measurement.

The serotonin blood level changes observed support the ability of the combined antioxidant in delivering serotonin across the gastrointestinal tract. Furthermore with respect to clinical efficacy, the percentage of patients with improvement of depression symptoms, premenstrual. syndrome, and migraine headaches, displays that these serotonin deficiency related illnesses may be beneficially affected b, the oral administration of scrotonin vitamin/dietary supplement.

I claim:

1. A method for the treatment of a patient suffering from premenstrual syndrome, depression, anemia, migraines or eating disorders which comprises: orally administering to said patient a therapeutic composition comprising: serotonin in an amount effective to increase the level of serotonin in the bloodstream to a supranormal level in combination with an antioxidant.

2. The method according to claim 1, wherein the composition comprises about 0.01 to 1.5 milligrams of serotonin.

3. The method according to claim 1, wherein the composition comprises, per unit dose, 20 to 1,000 milligrams of the antioxidant.

4. The method of claim 1 wherein the composition comprises: 1 to 20 parts by weight of the serotonin and 50 to 10,000 parts by weight of the antioxidant.

5. The method of claim 1 wherein said antioxidant is at least one vitamin selected from the group consisting of vitamin C, vitamin E and mixtures thereof.

6. A method for increasing the serotonin level in a human having a reduced serotonin level in their bloodstream: comprising orally administering to said human a composition comprising a serotonin in an amount effective to increase the serotonin level present in the bloodstream to a supranormal level, in combination with an antioxidant in an amount effective to prevent oxidation or degradation of the serotonin in the gastrointestinal tract.

7. The method of claim 6 wherein the antioxidant is selected from the group consisting of vitamin C, vitamin E and mixtures thereof.

8. The method of claim 6, wherein the composition comprises about 0.01 to 1.5 milligrams of serotonin per unit dose.

9. The method of claim 6, wherein the composition comprises about 20 to 1,000 milligrams of the antioxidant per unit dose.

10. The method of claim 6 wherein the composition comprises: 1 to 20 parts by weight of the serotonin or an equivalent amount of the pharmaceutically acceptable salt thereof, and 50 to 10,000 parts by weight of the antioxidant.

11. The method of claim 6 wherein the composition comprises: 1 to 20 parts by weight of the serotonin or an equivalent amount of the pharmaceutically acceptable salt of said serotonin, and 50 to 10,000 parts by weight of ascorbic acid or an equivalent amount of the pharmaceutically acceptable salt thereof.

* * * * *